(12) United States Patent
Baumann et al.

(10) Patent No.: US 6,265,352 B1
(45) Date of Patent: Jul. 24, 2001

(54) SUBSTITUTED CARBAMOYL TRIAZOLES AND THEIR USE AS HERBICIDES

(75) Inventors: Ernst Baumann, Dudenhofen; Cyrill Zagar, Ludwigshafen; Uwe Kardorff, Mannheim; Ulf Misslitz, Neustadt; Karl-Otto Westphalen, Speyer; Helmut Walter, Obrigheim; Gerhard Hamprecht, Weinheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/254,918

(22) PCT Filed: Sep. 9, 1997

(86) PCT No.: PCT/EP97/04902

§ 371 Date: Mar. 17, 1999

§ 102(e) Date: Mar. 17, 1999

(87) PCT Pub. No.: WO98/12193

PCT Pub. Date: Mar. 26, 1998

(30) Foreign Application Priority Data

Sep. 19, 1996 (DE) ................................ 196 38 245

(51) Int. Cl.⁷ ..................... A01N 41/02; A01N 43/30; A01N 43/653; C07D 261/04; C07D 413/02

(52) U.S. Cl. ................ 504/270; 504/271; 504/273; 504/274; 504/288; 504/294; 548/215; 548/240; 548/263.2; 548/264.2; 548/266.6; 548/266.8

(58) Field of Search .................. 504/273, 274, 504/270, 271, 288, 294; 548/263.2, 264.2, 266.6, 266.8, 215, 240

(56) References Cited

U.S. PATENT DOCUMENTS

| | | | |
|---|---|---|---|
| 4,006,244 | * 2/1977 | Siegle et al. | 424/282 |
| 5,308,830 | 5/1994 | Lopez | 504/273 |
| 5,521,186 | 5/1996 | Heeres et al. | 514/252 |

FOREIGN PATENT DOCUMENTS

| | | |
|---|---|---|
| 140 194 | 5/1985 | (EP). |
| 225 175 | 6/1987 | (EP). |
| 422 369 | 4/1991 | (EP). |

OTHER PUBLICATIONS

J. Med. Chem. 1992, 35, 3525–2536.
BE 863 151 (JP 61 178 930) Derwent (Jan. 24, 1977).
Derwent JP 7053529 (Aug. 10, 1993).

* cited by examiner

*Primary Examiner*—Jane C. Oswecki
(74) *Attorney, Agent, or Firm*—Keil & Weinkauf

(57) ABSTRACT

Substituted carbamoyltriazoles of the formula I as defined in the specification and the agriculturally useful salts thereof, processes for their preparation and their use as herbicides.

10 Claims, No Drawings

SUBSTITUTED CARBAMOYL TRIAZOLES AND THEIR USE AS HERBICIDES

This application is a 371 of PCT/EP97/04902 filed Sep. 9, 1997.

DESCRIPTION

The present invention relates to novel substituted carbamoyltriazoles of the formula I

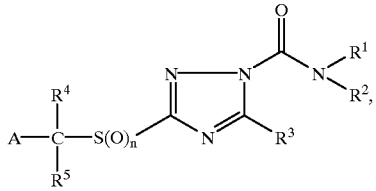

where:
- $R^1$ is hydrogen, $C_1$–$C_6$-alkyl, $C_1$–$C_6$-haloalkyl, $C_3$–$C_8$-cycloalkyl, $C_3$–$C_6$-alkenyl or $C_3$–$C_6$-alkynyl;
- $R^2$ is $C_1$–$C_6$-alkoxy or $C_1$–$C_6$-haloalkoxy or a radical listed under $R^1$; or
- $R^1$ and $R^2$ together form a $C_2$–$C_5$-alkanediyl radical which may carry one to three substituents selected from the group consisting of halogen and $C_1$–$C_6$-alkyl and, in the case of a $C_4$–$C_5$-alkanediyl radical, a $CH_2$ group may be replaced by oxygen or a group NH or N-$C_1$–$C_6$-alkyl;
- $R^3$,$R^4$ and $R^5$ are each hydrogen, cyano, $C_1$–$C_6$-alkyl, $C_1$–$C_6$-haloalkyl, $C_3$–$C_6$-cycloalkyl, $C_2$–$C_6$-alkenyl, $C_2$–$C_6$-alkynyl, $C_1$–$C_6$-alkoxy, $C_1$–$C_6$-haloalkoxy, $C_1$–$C_6$-alkylthio, $C_1$–$C_6$-alkylcarbonyl, $C_1$–$C_6$-haloalkylcarbonyl, $C_1$–$C_6$-alkoxycarbonyl, phenyl or benzyl, where the last two substituents may be partially or fully halogenated and may carry one to three of the following groups:
  - nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkoxycarbonyl;
- A is an unsubstituted or substituted saturated or partially unsaturated five or six-membered heterocycle containing one to three hetero atoms selected from the group consisting of oxygen, sulfur and nitrogen;
- n is 0, 1 or 2;
  - with the proviso that A is not 1,3-dioxolan-2-yl or 1,3-dioxan-2-yl;
  - and the agriculturally useful salts of I.

Furthermore, the invention relates to processes for preparing compounds of the formula I, to compositions comprising them and to their use for controlling harmful plants.

Carbamoyltriazoles are known from the literature, for example from EP-A 140 194, EP-A 422 369, U.S. Pat. No. 5,308,830, JP-A 07 053 529 and JP-A 61 178 930.

However, the herbicidal properties of the prior art compounds and the compatibility with crop plants are not fully satisfactory.

It is an object of the present invention to provide novel, in particular herbicidally active, compounds having improved properties and also novel intermediates, the triazoles of the formula II.

We have found that this object is achieved by the substituted carbamoyltriazoles of the formula I and their herbicidal activity and also by intermediates and processes for preparing the compounds I.

This invention further provides herbicidal compositions which comprise the compounds I and which have a very good herbicidal activity. It additionally provides processes for the preparation of these compositions and methods for controlling undesirable vegetation using the compounds I.

Depending on the substitution pattern, the compounds of the formula I can contain one or more chiral centers, in which case they exist in the form of enantiomer or diastereomer mixtures. This invention provides the pure enantiomers or diastereomers as well as their mixtures.

The compounds of the formula I may also be present in the form of their agriculturally useful salts, the kind of salt as a rule not being important. The salts of those cations or the acid addition salts of those acids are generally suitable whose cations or anions, respectively, do not interfere with the herbicidal activity of the compounds I. Suitable cations are in particular ions of the alkali metals, preferably sodium and potassium, of the alkaline earth metals, preferably calcium and magnesium, and of the transition metals, preferably manganese, copper, zinc and iron, and ammonium which, if desired, may carry one to four $C_1$–$C_4$-alkyl substituents and/or one phenyl or benzyl substituent, preferably diisopropylammonium, tetramethylammonium, tetrabutylammonium, trimethylbenzylammonium, and furthermore phosphonium ions, sulfonium ions, preferably tri ($C_1$–$C_4$-alkyl)sulfonium, and sulfoxonium ions, preferably tri ($C_1$–$C_4$-alkyl) sulfoxonium.

Anions of useful acid addition salts are primarily chloride, bromide, fluoride, hydrogen sulfate, sulfate, dihydrogenphosphate, hydrogenphosphate, nitrate, hydrogencarbonate, carbonate, hexafluorosilicate, hexafluorophosphate, benzoate and the anions of $C_1$–$C_4$-alkanoic acids, preferably formate, acetate, propionate and butyrate.

Preference is given to substituted carbamoyltriazoles of the formula I

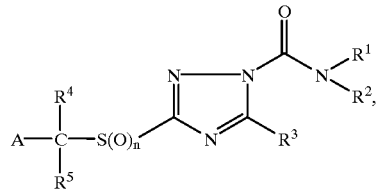

where:
- $R^1$ is hydrogen, $C_1$–$C_6$-alkyl, $C_1$–$C_6$-haloalkyl, $C_3$–$C_8$-cycloalkyl, $C_3$–$C_6$-alkenyl or $C_3$–$C_6$-alkynyl;
- $R^2$ is $C_1$–$C_6$-alkoxy or $C_1$–$C_6$-haloalkoxy, and the radicals mentioned under $R^1$; or
- $R^1$ and $R^2$ together form a $C_2$–$C_5$-alkanediyl radical which may carry one to three substituents selected from the group consisting of halogen and $C_1$–$C_6$-alkyl and, in the case of a $C_4$–$C_5$-alkanediyl radical, a $CH_2$ group may be replaced by oxygen or a group NH or N-$C_1$–$C_6$-alkyl;
- $R^3$,$R^4$ and $R^5$ are each hydrogen, cyano, $C_1$–$C_6$-alkyl, $C_1$–$C_6$-haloalkyl, $C_3$–$C_6$-cycloalkyl, $C_2$–$C_6$-alkenyl, $C_2$–$C_6$-alkynyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylcarbonyl, $C_1$–$C_6$-haloalkylcarbonyl, $C_1$–$C_6$-alkoxycarbonyl, phenyl or benzyl where the last two substituents may be partially or fully halogenated and may carry one to three of the following groups:
  - nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkoxycarbonyl;

A is a five-membered saturated or partially unsaturated heterocycle which contains one to three hetero atoms selected from the group consisting of oxygen, sulfur and nitrogen and which may carry, attached to carbon, one to three radicals selected from the group consisting of $R^6$, $R^7$ and $R^8$, and where any ring nitrogen may, independently of any other(s), carry a radical $R^{10}$; or is a six-membered saturated or partially unsaturated heterocycle which contains one to three hetero atoms selected from the group consisting of oxygen, sulfur and nitrogen and which may carry, attached to carbon, one to four radicals selected from the group consisting of $R^6$, $R^7$, $R^8$ and $R^9$, and where any ring nitrogen may, independently of any other(s), carry a radical $R^{10}$;

$R^6$, $R^7$, $R^8$ and $R^9$ are each cyano, halogen, $C_1$–$C_6$-alkyl, $C_1$–$C_6$-haloalkyl, $C_3$–$C_6$-cycloalkyl, $C_2$–$C_6$-alkenyl, $C_2$–$C_6$-alkynyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylcarbonyl, $C_1$–$C_6$-haloalkylcarbonyl, $C_1$–$C_6$-alkoxycarbonyl, phenyl or benzyl where the last two substituents may be partially or fully halogenated and/ or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkoxycarbonyl;

$R^{10}$ is $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkylcarbonyl, $C_1$–$C_6$-haloalkylcarbonyl, $C_1$–$C_6$-alkoxycarbonyl, phenyl or benzyl where the last two substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkoxycarbonyl;

n is 0, 1 or 2;

with the proviso that A is not 1,3-dioxolan-2-yl or 1,3-dioxan-2-yl;

and the agriculturally useful salts of I.

The organic moieties mentioned for the substituents $R^1$–$R^{10}$ or as radicals at phenyl rings are collective terms for individual listings of the individual group members. All hydrocarbon chains, ie. all the alkyl, haloalkyl, alkoxy, haloalkoxy, alkylthio, haloalkylthio, alkylcarbonyl, haloalkylcarbonyl, alkoxycarbonyl, cycloalkyl, alkanediyl, alkenyl and alkynyl moieties can be straight-chain or branched. If not stated otherwise, halogenated substituents preferably carry one to five identical or different halogens. The term halogen represents in each case fluorine, chlorine, bromine or iodine.

Other examples of meanings are:

$C_1$–$C_4$-alkyl and the alkyl moieties of $C_1$–$C_4$-alkylcarbonyl: methyl, ethyl, propyl, 1-methylethyl, butyl, 1-methylpropyl, 2-methylpropyl and 1,1-dimethylethyl;

$C_1$–$C_6$-alkyl, and the alkyl moieties of $C_1$–$C_6$-alkylcarbonyl: $C_1$–$C_4$-alkyl as mentioned above, and pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl, and the haloalkyl moieties of $C_1$–$C_4$-haloalkylcarbonyl: a $C_1$–$C_4$-alkyl radical as mentioned above which is partially or fully substituted by fluorine, chlorine, bromine and/or iodine, ie. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl, and the haloalkyl moieties of $C_1$–$C_6$-haloalkylcarbonyl: $C_1$–$C_4$-haloalkyl as mentioned above, and 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy, and the alkoxy moieties in $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;

$C_1$–$C_6$-alkoxy, and the alkoxy moieties in $C_1$–$C_6$-alkoxycarbonyl: $C_1$–$C_4$-alkoxy as mentioned above, and pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, ie. for example fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_6$-haloalkoxy: $C_1$–$C_4$-haloalkoxy as mentioned above, and 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$–$C_6$-alkylthio: methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$–$C_6$-haloalkylthio: a $C_1$–$C_6$-alkylthio radical as mentioned above, and which is partially or fully substituted by fluorine, chlorine, bromine and/or iodine, ie. for example fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio, nonafluorobutylthio, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio and dodecafluorohexylthio;

$C_2$–$C_5$-alkanediyl: ethane-1,2-diyl, propane-1,3-diyl, butane-1,3-diyl and pentane-1,5-diyl;

$C_3$–$C_6$-cycloalkyl: cyclopropyl, cyclobutyl, cyclopentyl and cyclohexyl;

$C_3$–$C_8$-cycloalkyl: a $C_3$–$C_6$-cycloalkyl radical as mentioned above, and cycloheptyl and cyclooctyl;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methyl-pent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl: a $C_3$–$C_6$-alkenyl radical as mentioned above, and ethenyl;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl: a $C_3$–$C_6$-alkynyl radical as mentioned above, and ethynyl;

Preferred with a view to the biological activity are those substituted carbamoyltriazoles of the formula I where, alone or in combination:

$R^1$ is $C_1$–$C_6$-alkyl, $C_1$–$C_6$-haloalkyl, $C_3$–$C_8$-cycloalkyl, $C_3$–$C_6$-alkenyl or $C_3$–$C_6$-alkynyl; particularly preferably $C_1$–$C_4$-alkyl such as methyl, ethyl, propyl or isopropyl, $C_1$–$C_4$-haloalkyl such as fluoromethyl, difluoromethyl or 2,2,2-trifluoroethyl, $C_3$–$C_6$-cycloalkyl such as cyclopropyl, cyclopentyl or cyclohexyl, $C_3$–$C_4$-alkenyl such as 2-propenyl, 2-butenyl, 3-butenyl or 1-methyl-2-propenyl or $C_3$–$C_4$-alkynyl such as 2-propynyl; very particularly preferably methyl, ethyl, propyl or isopropyl;

$R^2$ is $C_1$–$C_6$-alkyl, $C_1$–$C_6$-haloalkyl, $C_3$–$C_8$-cycloalkyl, $C_3$–$C_6$-alkenyl, $C_3$–$C_6$-alkynyl, $C_1$–$C_6$-alkoxy or $C_1$–$C_6$-haloalkoxy; particularly preferably $C_1$–$C_4$-alkyl such as methyl, ethyl, propyl or isopropyl, $C_1$–$C_4$-haloalkyl such as fluoromethyl, difluoromethyl or 2,2,2-trifluoroethyl, $C_3$–$C_6$-cycloalkyl such as cyclopropyl, cyclopentyl or cyclohexyl, $C_3$–$C_4$-alkenyl such as 2-propenyl, 2-butenyl, 3-butenyl or 1-methyl-2-propenyl, $C_3$–$C_4$-alkynyl such as 2-propynyl, $C_1$–$C_4$-alkoxy such as methoxy or ethoxy or $C_1$–$C_4$-haloalkoxy such as difluoromethoxy; very particularly preferably methyl, ethyl, propyl or isopropyl;

or $R^1$ and $R^2$ together form an ethane-1,2-diyl, propane-1,3-diyl, butane-1,4-diyl, pentane-1,5-diyl or 3-oxapentane-1,5-diyl radical which may carry one to three $C_1$–$C_6$-alkyl substituents;

particularly preferably propane-1,3-diyl, butane-1,4-diyl, pentane-1,5-diyl or 3-oxapentane-1,5-diyl;

$R^3$ is hydrogen, cyano, $C_1$–$C_6$-alkyl, $C_1$–$C_6$-haloalkyl, $C_3$–$C_6$-cycloalkyl, $C_2$–$C_6$-alkenyl, $C_2$–$C_6$-alkynyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylcarbonyl, $C_1$–$C_6$-haloalkylcarbonyl, $C_1$–$C_6$-alkoxycarbonyl, phenyl or benzyl; particularly preferably hydrogen, cyano, $C_1$–$C_4$-alkyl such as methyl or ethyl, $C_1$–$C_4$-haloalkyl such as trifluoromethyl, $C_3$–$C_6$-cycloalkyl such as cyclopropyl, $C_3$–$C_4$-alkynyl such as prop-1-yn-3-yl, $C_3$–$C_4$-alkenyl such as prop-1-en-3-yl, $C_1$–$C_4$-alkoxy such as ethoxy, $C_1$–$C_4$-haloalkoxy such as difluoromethoxy, $C_1$–$C_4$-alkylthio such as methylthio, $C_1$–$C_4$-alkylcarbonyl such as methylcarbonyl, $C_1$–$C_4$-alkoxy-carbonyl such as ethoxycarbonyl, phenyl or benzyl;

$R^4$ and $R^5$ are each hydrogen, $C_1$–$C_6$-alkyl, $C_1$–$C_6$-haloalkyl, $C_3$–$C_6$-cycloalkyl, $C_2$–$C_6$-alkenyl, $C_2$–$C_6$-alkynyl, $C_1$–$C_6$-alkoxy or $C_1$–$C_6$-haloalkoxy; particularly preferably hydrogen, $C_1$–$C_4$-alkyl such as methyl or ethyl, $C_1$–$C_4$-haloalkyl such as trifluoromethyl, $C_3$–$C_6$-cycloalkyl such as cyclopropyl, $C_3$–$C_4$-alkynyl such as prop-1-yn-3-yl, $C_3$–$C_4$-alkenyl such as prop-1-en-3-yl, $C_1$–$C_4$-alkoxy such as ethoxy or $C_3$–$C_4$-alkenyl such as difluoromethoxy;

is tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-dioxathiolan-4-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl, 3,4-dihydropyrimidin-6-yl, where the sulfur of the heterocycles mentioned may be oxidized to S=O or S(=O)$_2$ and where the five-membered ring or six-membered ring is unsubstituted.

Also preferred with a view to the biological activity are carbamoyltriazoles of the formula I where $R^1$ to $R^5$ and A are as defined for the compounds mentioned above and A may additionally be 1,3-dioxolan-2-yl and 1,3-dioxan-2-yl and where the sulfur of the heterocycles mentioned may be oxidized to S=O or S(=O)$_2$ and where one of the abovementioned five-membered heterocycles carries, attached to carbon, one to three radicals selected from the group consisting of $R^6$, $R^7$ and $R^8$ and where any ring nitrogen may, independently of any other(s), carry a radical $R^{10}$ and where one of the abovementioned six-membered heterocycles carries, attached to carbon, one to four radicals selected from the group consisting of $R^6$, $R^7$, $R^8$ and $R^9$ and where any ring nitrogen may, independently of any other(s), carry a radical $R^{10}$;

$R^6$, $R^7$, $R^8$ and $R^9$ are each cyano, halogen, $C_1$–$C_6$-alkyl, $C_1$–$C_6$-haloalkyl, $C_3$–$C_6$-cycloalkyl, $C_2$–$C_6$-alkenyl, $C_2$–$C_6$-alkynyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylcarbonyl, $C_1$–$C_6$-haloalkylcarbonyl, $C_1$–$C_6$-alkoxycarbonyl, phenyl or benzyl, where the last two substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkoxycarbonyl;

$R^{10}$ is $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkylcarbonyl, $C_1$–$C_6$-haloalkylcarbonyl, $C_1$–$C_6$-alkoxycarbonyl, phenyl or benzyl, where the last two substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkoxycarbonyl.

Very particular preference is given to the substituted carbamoyltriazoles of the formula Ia (= I where n=0), in particular to the compounds of Table 1:

TABLE 1*)

(structure Ia: A-C(R⁴)(R⁵)-S-[1,2,4-triazole with R³]-C(=O)-N(R¹)(R²), where n = 0)

| No. | A | R¹ | R² | R³ | R⁴ | R⁵ |
|---|---|---|---|---|---|---|
| Ia.01 | pyrrolidin-2-yl (NH) | $C_2H_5$ | $C_2H_5$ | H | H | H |
| Ia.02 | 1-methylpyrrolidin-3-yl | $C_2H_5$ | $C_2H_5$ | H | $CH_3$ | H |
| Ia.03 | tetrahydrothiophen-2-yl | $C_2H_5$ | $C_2H_5$ | H | $CF_3$ | H |
| Ia.04 | tetrahydrothiophen-3-yl | $C_2H_5$ | $C_2H_5$ | H | cyclopropyl | H |
| Ia.05 | tetrahydrothiophen-2-yl S-oxide | $C_2H_5$ | $C_2H_5$ | H | -CH₂-CH=CH₂ | H |
| Ia.06 | tetrahydrothiophen-3-yl S,S-dioxide | $C_2H_5$ | $C_2H_5$ | H | -CH₂-C≡CH | H |
| Ia.07 | tetrahydrofuran-2-yl | $C_2H_5$ | $C_2H_5$ | H | $OC_2H_5$ | H |
| Ia.08 | tetrahydrofuran-3-yl | $C_2H_5$ | $C_2H_5$ | H | $OCHF_2$ | H |
| Ia.09 | 4,5-dihydro-1H-pyrazol-4-yl | $C_2H_5$ | $C_2H_5$ | H | $CH_3$ | $CH_3$ |

TABLE 1*)-continued

Ia (where n = 0)

| No. | A | R¹ | R² | R³ | R⁴ | R⁵ |
|---|---|---|---|---|---|---|
| Ia.10 | 1-methyl-pyrazolin-5-yl | $C_2H_5$ | $C_2H_5$ | H | H | $CF_3$ |
| Ia.11 | isoxazolin-5-yl | $C_2H_5$ | $C_2H_5$ | H | H | cyclopropyl |
| Ia.12 | isothiazolin-4-yl | $C_2H_5$ | $C_2H_5$ | H | H | allyl |
| Ia.13 | 4-methyl-1,3-dioxolan-2-yl | $C_2H_5$ | $C_2H_5$ | H | H | propargyl |
| Ia.14 | 1,3-oxathiolan-2-yl | $C_2H_5$ | $C_2H_5$ | H | H | $OC_2H_5$ |
| Ia.15 | 1,3-dithiolan-2-yl | $C_2H_5$ | $C_2H_5$ | H | H | $OCHF_2$ |
| Ia.16 | imidazolidin-4-yl | $CH_3$ | $CH_3$ | H | H | H |
| Ia.17 | 4,4-dimethyl-oxazolidin-2-yl | $CH_3$ | $OCH_3$ | H | H | H |
| Ia.18 | thiazolidin-2-yl | isopropyl | isopropyl | H | H | H |
| Ia.19 | 2,3-dihydrofuran-5-yl | cyclopentyl | cyclopentyl | H | H | H |
| Ia.20 | 2,3-dihydrothiophen-3-yl | $CH_2CF_3$ | $CH_2CF_3$ | H | H | H |

TABLE 1*)-continued

[Structure Ia: A-C(R4)(R5)-S-[1,2,4-triazole with R3]-C(=O)-N(R1)(R2), where n = 0]

| No. | A | R¹ | R² | R³ | R⁴ | R⁵ |
|-----|---|----|----|----|----|----|
| Ia.21 | 4,5-dihydro-2-oxazolyl (N=CH-O-CH2-CH) variant — 2-pyrroline-like (N=CH-CH2-CH) | CH2-CH=CH- | $C_2H_5$ | H | H | H |
| Ia.22 | 4,5-dihydrooxazol-2-yl | CH2-C≡CH | $CH_3$ | H | H | H |
| Ia.23 | 4,5-dihydroisothiazol-5-yl | $C_2H_5$ | $C_2H_5$ | CN | H | H |
| Ia.24 | 4,5-dihydro-1H-pyrazol-4-yl | $C_2H_5$ | $C_2H_5$ | $CH_3$ | H | H |
| Ia.25 | 4,5-dihydro-1H-imidazol-4-yl | $C_2H_5$ | $C_2H_5$ | $CF_3$ | H | H |
| Ia.26 | oxazol-2-yl (4,5-dihydro) | $C_2H_5$ | $C_2H_5$ | cyclopropyl | H | H |
| Ia.27 | 4,5-dihydrothiazol-2-yl | $C_2H_5$ | $C_2H_5$ | CH2-CH=CH2 | H | H |
| Ia.28 | 2,5-dihydrofuran-2-yl | $C_2H_5$ | $C_2H_5$ | CH2-C≡CH | H | H |
| Ia.29 | tetrahydropyran-2-yl | $C_2H_5$ | $C_2H_5$ | $OC_2H_5$ | H | H |
| Ia.30 | tetrahydropyran-3-yl | $C_2H_5$ | $C_2H_5$ | $OCHF_2$ | H | H |
| Ia.31 | tetrahydropyran-4-yl | $C_2H_5$ | $C_2H_5$ | $SCH_3$ | H | H |

TABLE 1*)-continued

![Structure Ia: A-C(R4)(R5)-S-[1,2,4-triazole with R3]-C(=O)-N(R1)(R2)]

(where n = 0)

| No. | A | R¹ | R² | R³ | R⁴ | R⁵ |
|---|---|---|---|---|---|---|
| Ia.32 | 2-tetrahydrothiopyranyl | C₂H₅ | C₂H₅ | –C(=O)CH₃ | H | H |
| Ia.33 | 3-(1-oxo-tetrahydrothiopyranyl) | C₂H₅ | C₂H₅ | –C(=O)OC₂H₅ | H | H |
| Ia.34 | 4-(1,1-dioxo-tetrahydrothiopyranyl) | C₂H₅ | C₂H₅ | C₆H₅ | H | H |
| Ia.35 | 2-piperidinyl | C₂H₅ | C₂H₅ | CH₂—C₆H₅ | H | H |
| Ia.36 | 2-hexahydropyrimidinyl | ----CH₂—CH₂---- | | H | H | H |
| Ia.37 | 2-(5,5-dimethyl-1,3-dioxanyl) | ----CH₂—CH₂—CH₂---- | | H | H | H |
| Ia.38 | 2-(1,3-oxathianyl) | ----CH₂—CH₂—CH₂—CH₂---- | | H | H | H |
| Ia.39 | 2-(1,3-dithianyl) | CH₃ | CH₃ | H | H | H |
| Ia.40 | 2-methyl-1,3-dioxan-5-yl | CH₃ | OCH₃ | H | H | H |
| Ia.41 | 3-morpholinyl | CH₂—CH=CH– | C₂H₅ | H | H | H |
| Ia.42 | 4-(3,4-dihydro-2H-pyranyl) | CH₂—C≡C– | CH₃ | H | H | H |

TABLE 1*)-continued

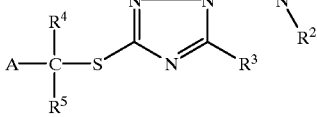

(where n = 0)

| No. | A | R¹ | R² | R³ | R⁴ | R⁵ |
|---|---|---|---|---|---|---|
| Ia.43 | 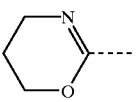 | $C_2H_5$ | $C_2H_5$ | CN | H | H |
| Ia.44 | 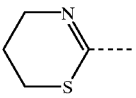 | $C_2H_5$ | $C_2H_5$ | $CH_3$ | H | H |
| Ia.45 | 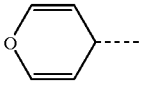 | $C_2H_5$ | $C_2H_5$ | $CF_3$ | H | H |
| Ia.46 | 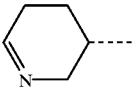 | $C_2H_5$ | $C_2H_5$ |  | H | H |
| Ia.47 | 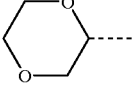 | $C_2H_5$ | $C_2H_5$ | 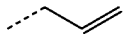 | H | H |
| Ia.48 | 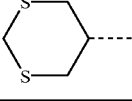 | $C_2H_5$ | $C_2H_5$ | 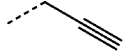 | H | H |

*)The dotted line indicates the bonding position in each case.

Furthermore, very particular preference is given to the substituted carbamoyltriazoles of the formula Ib, in particular to the compounds Ib.01–Ib.48, which differ from the compounds Ia.01–Ia.48 in that n is 1:

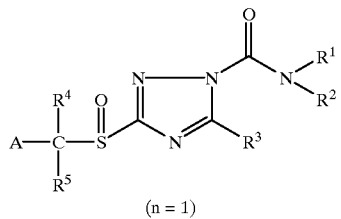

(Ib)

(n = 1)

Also, very particular preference is given to the substituted carbamoyltriazoles of the formula Ic, in particular to the compounds Ic.01–Ic.48, which differ from the compounds Ia.01–Ia.48 in that n is 2:

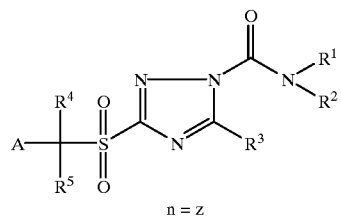

Ic n = z

Most particularly preferred are the substituted carbamoyltriazoles of the formula Ic, in particular the compounds Ic.01–Ic.48 as listed above.

Particularly preferred are also substituted carbamoyltriazoles of the formula I where R¹ and R² are each $C_1$–$C_6$-alkyl.

Also particularly preferred are substituted carbamoyltriazoles of the formula I where R³ and R⁴ are each hydrogen.

Also particularly preferred are substituted carbamoyltriazoles of the formula I where A is a saturated or partially unsaturated five- or six-membered heterocycle with or without substitution which contains one hetero atom, i.e. for example tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothienyl-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-2H-pyrrol-4-yl, 3,4-dihydro-2H-pyrrol-5-yl, tetrahydropyran-2-yl, tetrahydro-pyran-3-yl, tetrahydropyran-4-yl, tetrahydrothiopyran-2-yl, tetrahydrothiopyran-3-yl, tetrahydrothiopyran-4-yl, piperidin-2-yl, piperidin-3-yl, piperidin-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 2H-pyran-2-yl, 2H-pyran-3-yl, 2H-pyran-4-yl, 2H-pyran-5-yl, 2H-pyran-6-yl, 4H-thiopyran-2-yl, 4H-thiopyran-3-yl, 4H-thiopyran-4-yl, 2H-thiopyran-2-yl, 2H-thiopyran-3-yl, 2H-thiopyran-4-yl, 2H-thiopyran-5-yl, 2H-thiopyran-6-yl, 1,4-dihydropyridin-2-yl, 1,4-dihydropyridin-3-yl, 1,4-dihydropyridin-4-yl, 1,2-dihydropyridin-2-yl, 1,2-dihydropyridin-3-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, where the abovementioned five-membered heterocycles may carry one to three carbon-attached radicals selected from the group $R^6$, $R^7$ and $R^8$, the ring nitrogen opt. carrying the radical $R^{10}$, and where the abovementioned six-membered heterocycles may carry one to four carbon-attached radicals selected from the group $R^6$, $R^7$, $R^8$ and $R^9$, the ring nitrogen opt. carrying the radical $R^{10}$, and/or where the sulfur of the mentioned heterocycles may, if appropriate, be oxidized to S=O or S(=O)$_2$.

Most particularly preferred are substituted carmaboyltriazoles of the formula I where A is a saturated or partially unsaturated five- or six-membered heterocycle with or without substitution which contains one oxygen hetero atom, ie. for example tetrahydrofuran-2-yl, tetrahydrofuran-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, tetrahydropyran-2-yl, tetrahydropyran-3-yl, tetrahydropyran-4-yl, 2H-3,4-dihydropyran-6-yl, 2H-3, 4-dihydropyran-5-yl, 2H-3,4-dihydropyran-4-yl, 2H-3,4-dihydropyran-3-yl, 2H-3,4-dihydropyran-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 4H-pyran-2-yl, 4H-pyran-3-yl, 4H-pyran-4-yl, 2H-pyran-2-yl 2H-pyran-3-yl, 2H-pyran-4-yl, 2H-pyran-5-yl or 2H-pyran-6-yl, where the abovementioned five-membered heterocycles may carry one to three carbon-attached radicals selected from the group $R^6$, $R^7$ and $R^8$, and where the abovementioned six-membered heterocycles may carry one to four carbon-attached radicals selected from the group $R^6$, $R^7$, $R^8$ and $R^9$.

Also particularly preferred are substituted carbamoyltriazoles of the formula I where A is a saturated or partially unsaturated five- or six-membered heterocycle with or without substitution which contains two hetero atoms except for 1,3-dioxolan-2-yl and 1,3-dioxan-2-yl.

Most particularly preferred are substituted carbamoyltriazoles of the formula I where A is a saturated or partially unsaturated five- or six-membered heterocycle with or without substitution which contains two hetero atoms and where not more than one hetero atom is attached adjacent to the bonding position, ie. tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-4-yl, tetrahydrooxazol-4-yl, tetrahydrooxazol-5-yl, tetrahydrothiazol-4-yl, tetrahydrothiazol-5-yl, 1,3-dioxolan-4-yl, 1,3-oxathiolan-4-yl, 1,3-oxathiolan-5-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-4-yl, 4,5-dihydro-1H-imidazol-5-yl, 2,5-dihydro-1H-imidazol-4-yl, 2,5-dihydro-1H-imidazol-5-yl, 2,3-dihydro-1H-imidazol-4-yl, 4,5-dihydrooxazol-4-yl, 4,5-dihydrooxazol-5-yl, 2,5-dihydrooxazol-4-yl, 2,5-dihydrooxazol-5-yl, 2,3-dihydrooxazol-4-yl, 2,3-dihydrooxazol-5-yl, 4,5-dihydrothiazol-4-yl, 4,5-dihydrothiazol-5-yl, 2,5-dihydrothiazol-4-yl, 2,5-dihydrothiazol-5-yl, 2,3-dihydrothiazol-4-yl, 2,3-dihydrothiazol-5-yl, 1,3-dioxol-4-yl, 1,3-dithiol-4-yl, 1,3-oxathiol-4-yl, 1,3-oxathiol-5-yl, 1,3-dioxan-4-yl, 1,3-dioxan-5-yl, 1,4-dioxan-2-yl, 1,3-dithian-4-yl, 1,3-dithian-5-yl, 1,4-dithian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-4-yl, tetrahydro-1,3-oxazin-5-yl, tetrahydro-1,3-oxazin-6-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-4-yl, 2H-1,3-oxazin-5-yl, 2H-1,3-oxazin-6-yl, 2H-1,3-thiazin-4-yl, 2H-1,3-thiazin-5-yl, 2H-1,3-thiazin-6-yl, 4H-1,3-oxazin-4-yl, 4H-1,3-oxazin-5-yl, 4H-1,3-oxazin-6-yl, 4H-1,3-thiazin-4-yl, 4H-1,3-thiazin-5-yl, 4H-1,3-thiazin-6-yl, 6H-1,3-oxazin-4-yl, 6H-1,3-oxazin-5-yl, 6H-1,3-oxazin-6-yl, 6H-1,3-oxazin-4-yl, 6H-1,3-oxazin-5-yl, 6H-1,3-oxazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-4-yl, 1,4-dihydropyrimidin-5-yl, 1,4-dihydropyrimidin-6-yl, 3,4-dihydropyrimidin-4-yl, 3,4-dihydropyrimidin-5-yl or 3,4-dihydropyrimidin-6-yl, where the abovementioned five-membered heterocycles may carry one to three carbon-attached radicals selected from the group $R^6$, $R^7$ and $R^8$, each of the ring nitrogens, if appropriate, independently of the other optionally carrying a radical $R^{10}$, and where the abovementioned six-membered heterocycles may carry one to four carbon-attached radicals selected from the group $R^6$, $R^7$, $R^8$ and $R^9$, and each of the ring nitrogens, if appropriate, independently of the other opt. carrying a radical $R^{10}$ and/or where the sulfur of the mentioned heterocycles may, if appropriate, be oxidized to S=O or S(=O)$_2$.

Also most particularly preferred are substituted carbamoyltriazoles of the formula I where A is tetrahydroimidazol-2-yl, tetrahydrooxazol-2-yl, tetrahydrothiazol-2-yl, 1,3-oxathiolan-2-yl, 1,3-dithiolan-2-yl, 4,5-dihydro-1H-imidazol-2-yl, 2,5-dihydro-1H-imidazol-2-yl, 2,3-dihydro-1H-imidazol-2-yl, 4,5-dihydrooxazol-2-yl, 2,5-dihydrooxazol-2-yl, 2,3-dihydrooxazol-2-yl, 4,5-dihydrothiazol-2-yl, 2,5-dihydrothiazol-2-yl, 2,3-dihydrothiazol-2-yl, 1,3-dithiol-2-yl, 1,3-oxathiol-2-yl, 1,3-dithian-2-yl, 1,3-oxathian-2-yl, hexahydropyrimidin-2-yl, tetrahydro-1,3-oxazin-2-yl, tetrahydro-1,3-thiazin-2-yl, 4H-5,6-dihydro-1,3-oxazin-2-yl, 4H-5,6-dihydro-1,3-thiazin-2-yl, 3,4,5,6-tetrahydropyrimidin-2-yl, 1,2,3,4-tetrahydropyrimidin-2-yl, 2H-1,3-oxazin-2-yl, 2H-1,3-thiazin-2-yl, 4H-1,3-oxazin-2-yl, 4H-1,3-thiazin-2-yl, 6H-1,3-oxazin-2-yl, 6H-1,3-thiazin-2-yl, 2,3-dihydropyrimidin-2-yl, 2,5-dihydropyrimidin-2-yl, 3,4-dihydropyrimidin-2-yl or 4,5-dihydropyrimidin-2-yl, where the abovementioned five-membered heterocycles may carry one to three carbon-attached radicals selected from the group $R^6$, $R^7$ and $R^8$, each ring nitrogen, if appropriate, independently of the others optionally carrying a radical $R^{10}$, and where the abovementioned six-membered heterocycles may carry one to four carbon-attached radicals selected from the group $R^6$, $R^7$, $R^8$ and $R^9$, each of the ring nitrogens, if appropriate, independently of the others optionally carrying a radical $R^{10}$, and/or where the sulfur of the mentioned heterocycles may, if appropriate, be oxidized to S=O or S (=O)$_2$.

Also most particularly preferred are substituted carbamoyltriazoles of the formula I where A is 1,3-dioxolan-2-yl, 1,3-dioxol-2-yl or 1,3-dioxan-2-yl, where the abovementioned five-membered heterocycles carry one to three carbon-attached radicals selected from the group $R^6$, $R^7$ and $R^8$, and where the abovementioned six-membered heterocycles carry one to four carbon-attached radicals selected from the group $R_6$, $R^7$, $R^8$ and $R^9$.

Also particularly preferred are substituted carbamoyltriazoles of the formula I where:

$R^1$ and $R^2$ are ethyl $R^3$ is hydrogen $R^4$ is hydrogen $R^5$ is hydrogen or methyl A is tetrahydrofuran-2-yl, tetrahydrofuran-3-yl, tetrahydrothien-3-yl, tetrahydroisoxazol-5-yl, 1,3-dioxolan-4-yl, 4,5-dihydroisoxazol-5-yl, tetrahydropyran-2-yl, tetrahydropyran-3-yl, tetrahydropyran-4-yl, tetrahydrothiopyran-3-yl, tetrahydrothiopyran-4-yl, 2H-3,4-dihydropyran-4-yl or 2H-5,6-dihydrothiopyran-3-yl, where the abovementioned heterocycles may be unsubstituted or substituted by one or two radicals selected from the following group: $C_1$–$C_6$-alkyl, $C_1$–$C_6$-alkoxy, phenyl or benzyl which in turn may be partially or fully halogenated and may carry one to three substituents of the following group: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkoxycarbonyl, and where the sulfur of the heterocycles may be oxidized to S=O or S(=O)$_2$; 1,3-dioxan-2-yl which is substituted by one or two $C_1$–$C_6$-alkyl radicals;

n is 0 or 2.

The substituted carbamoyltriazoles of the formula I can be obtained in a variety of ways, for example by one of the processes below:

Process A

Reaction of a triazole of the formula II with a carbamoyl halide of the formula III

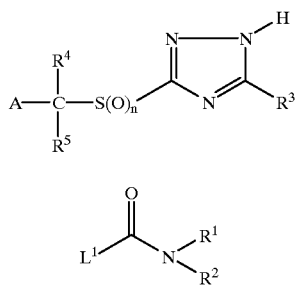

$L^1$ is halogen, preferably chlorine.

As a rule, the reaction is carried out in an inert organic solvent. Suitable inert organic solvents are, for example, aromatic hydrocarbons, such as benzene or toluene, halogenated hydrocarbons, such as methylene chloride, 1,2-dichloroethane or chlorobenzene, ethers, such as diethyl ether, methyl tert-butyl ether, tetrahydrofuran or dioxane, ketones, such as acetone or methyl ethyl ketone, or polar solvents, such as dimethylformamide, diethylformamide or dimethyl sulfoxide, or mixtures thereof.

It may be advantageous to carry out the reaction in the presence of a base. Suitable bases are, inter alia, alkali metal alkoxides, in particular sodium methoxide or sodium ethoxide, alkali metal hydroxides, in particular sodium hydroxide or potassium hydroxide, alkali metal carbonates, in particular sodium carbonate or potassium carbonate, metal hydrides, such as sodium hydride, organic bases, for example amines, such as triethylamine, pyridine or N,N-dimethylaminopyridine, or mixtures thereof.

As a rule, the starting materials are employed in equimolar amounts. However, it may be advantageous to employ an excess of one or the other component.

The amount of the base is preferably 0.5 to two times the molar amount, based on the starting materials.

The reaction temperature is generally in the range from 0° C. to the boiling point of the reaction mixture.

Process B

Reaction of substituted carbamoyltriazoles of the formula I where n=0,

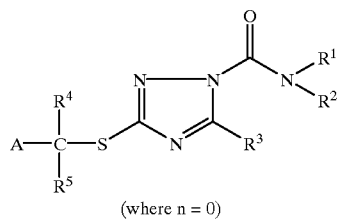

(where n = 0)

with oxidizing agents to give substituted carbamoyltriazoles of the formula I where n=1 or 2.

Suitable oxidizing agents are, inter alia, organic peroxides, such as m-chloroperbenzoic acid, peroxyacetic acid or trifluoroperoxyacetic acid, and inorganic peroxides, such as hydrogen peroxide or sodium periodate.

It may also be advantageous to add catalysts, such as tungstates.

Depending on the oxidizing agent, suitable solvents are aromatic hydrocarbons, such as benzene or toluene, halogenated hydrocarbons, such as methylene chloride, chloroform, 1,2-dichloroethane or chlorobenzene, organic acids, such as acetic acid, propionic acid or trifluoroacetic acid, or mixtures thereof.

The oxidizing agent can be employed in an equimolar amount, based on the starting material; although it may be advantageous to use an excess of up to 10 molar equivalents. Generally, the oxidation catalyst is employed in a ratio of 1 to 20 mol %, based on the starting material.

The reaction temperature is usually in the range of from 0° C. to the boiling point of the reaction mixture.

The triazoles of the formula II are novel, the meanings being as defined above.

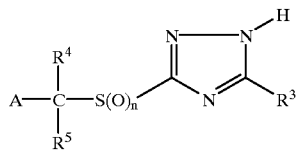

The particularly preferred embodiments of the triazoles of the formula II as regards the variables $R^1$ to $R^5$ correspond to those of the substituted carbamoyltriazoles of the formula I.

The preparation of the compounds of the formula II where n=0 is carried out for example by reacting a mercaptotriazole of the formula IV

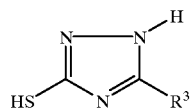

with a compound of the formula V,

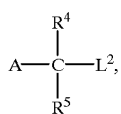

where $L^2$ is a nucleophilically displaceable leaving group, such as halogen, for example chlorine or bromine, $C_1$–$C_6$-alkylsulfonyloxy, for example mesylate, $C_1$–$C_6$-haloalkylsulfonyloxy, for example triflate, or arylsulfonyloxy, for example tosylate.

These compounds are synthesized similarly to the conditions described under Process A.

The compounds of the formula II where n=1 or 2 are synthesized by oxidizing compounds of the formula II where n=0 according to the conditions described under Process B.

Work-up of the reaction mixtures is generally carried out by methods known per se, for example by removing the solvent, partitioning the residue in a mixture of water and organic solvent and work-up of the organic phase to afford the product.

Preparation Examples

Example 1

1-Diethylcarbamoyl-3-(tetrahydropyran-2-yl)-methylsulfonyl-1,2,4-triazole (Compound 2.02)

a) Tetrahydropyran-2-ylmethyl methanesulfonate

In 200 ml of toluene, 23.2 g (200 mmol) of tetrahydropyran-2-ylmethanol were admixed with 27.5 g (240 mmol) of methanesulfonyl chloride. At 10° C., 24.3 g (240 mmol) of triethylamine were then added dropwise, and stirring was continued for 2 hours at room temperature. 200 ml of methyl tert-butyl ether and 200 ml of water were then added to the mixture and the organic phase was separated off, washed with 200 ml of water and dried. Removal of the solvent under reduced presure gave 33.7 g (87% of theory) of a clear oil. ($^1$H-NMR (CDCl$_3$; δ in ppm): 4.20 (d,2H); 4.05 (dd,1H); 3.60 (m,1H); 3.45 (m,1H); 3.1 (s,3H); 1.95 (m,1H); 1.45 (m,5H))

b) 3-(Tetrahydropyran-2-yl)methylthio-1,2,4-triazole 9.7 g (173 mmol) of potassium hydroxide and 17.5 g (173 mmol) of 3-mercapto-1,2,4-triazole were dissolved in 200 ml of methanol and heated under reflux for one hour. After the solvent had been distilled off under reduced pressure, the residue was dried by azeotropic distillation with toluene and then taken up in 300 ml of methanol. 33.6 g (173 mmol) of tetrahydropyran-2-ylmethyl methanesulfonate (step a) were then added and the mixture was stirred at room temperature for 24 hours. 200 ml of water and 200 ml of methyl tert-butyl ether were then added to the reaction mixture and the organic phase was separated off, washed with water and dried. The mixture was concentrated and the residue was chromatographed over silica gel, yielding 18.2 g (53% of theory) of a yellow oil. ($^1$H-NMR (CDCl$_3$; δ in ppm): 8.05 (s,1H); 4.15 (d,1H); 3.65 (m,1H); 3.50 (m,1H); 3.25–3.10 (m,2H); 1.85 (m,1H); 1.75–1.25 (m,6H))

c) 1-Diethylcarbamoyl-3-(tetrahydropyran-2-yl)methylthio-1,2,4-triazole (Compound 2.01)

11.6 g (85 mmol) of diethylcarbamoyl chloride and a spatula-tipful of dimethylaminopyridine were added to a solution of 200 ml of absolute tetrahydrofuran and 17.0 g (85 mmol) of 3-(tetrahydropyran-2-yl)methylthio-1,2,4-triazole (step b). 9.5 g (94 mmol) of triethylamine were then added dropwise and the mixture was heated under reflux for 2 hours. The solvent was distilled off and the residue was purified by chromatography over silica gel. 11.2 g (44% of theory) of a viscous clear oil were obtained. ($^1$H-NMR (CDCl$_3$; δ in ppm): 8.75 (s,1H); 4.00 (d,1H); 3.70–3.50 (bm,5H); 3.40 (dt,1H); 3.25 (d,2H); 1.85 (d,1H); 1.80 (d,1H); 1.65–1.45 (m,4H); 1.30 (t,6H))

d) 1-Diethylcarbamoyl-3-(tetrahydropyran-2-yl) methylsulfonyl-1,2,4-triazole 5.0 g (17 mmol) of 1-diethylcarbamoyl-3-(tetrahydropyran-2-yl)methylthio-1–2,4-triazole (step c) were dissolved in 100 ml of glacial acetic acid and admixed with a spatula-tipful of sodium tungstate. At 50° C., 4.8 g (42 mmol) of hydrogen peroxide (30% strength solution in water) were then added dropwise and the mixture was heated under reflux for 2 hours. After cooling, 100 ml of water and 100 ml of dichloromethane were added to the reaction mixture and the organic phase was washed with sodium dithionite solution and then with sodium bicarbonate solution, and dried. The solution was concentrated and the residue was digested with a little diethyl ether and filtered off under suction. 3.0 g (50% of theory) of a white crystalline powder (melting point 122° C.) were obtained. ($^1$H-NMR (CDCl$_3$; δ in ppm): 8.85 (s,1H)); 3.95 (m,1H); 3.70 (m,2H); 3.70–3.50 (bm,4H); 3.35 (m,2H); 1.85 (m,1H); 1.70 (dd, 1H); 1.55–1.40 (m,4H); 1.30 (d,6H).

The substituted carbamoyltriazole of the formula I described above and other carbamoyltriazoles of the formula I which have been or can be prepared in a similar manner or in a manner known per se are listed in Table 2:

TABLE 2*)

I (structure shown: A—CH(R$^5$)—S(O)$_n$— connected to 1,2,4-triazole bearing a C(=O)N(C$_2$H$_5$)$_2$ group)

(where $R^1$, $R^2$ = $C_2H_5$ and $R^3$, $R^4$ = H)

| No. | A | R$^5$ | n | mp [° C.] |
|---|---|---|---|---|
| 2.01 | tetrahydropyran-2-yl | H | 0 | oil |
| 2.02 | tetrahydropyran-2-yl | H | 2 | 122 |
| 2.03 | tetrahydropyran-3-yl | H | 0 | oil |
| 2.04 | tetrahydropyran-3-yl | H | 2 | 88–89 |

TABLE 2*)-continued
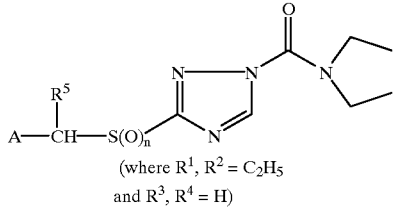
(where R¹, R² = C₂H₅ and R³, R⁴ = H)
| No. | A | R⁵ | n | mp [° C.] |
|---|---|---|---|---|
| 2.05 | | H | 0 | oil |
| 2.06 | | H | 2 | oil |
| 2.07 | | H | 0 | oil |
| 2.08 | | H | 2 | 102–105 |
| 2.09 | | H | 0 | oil |
| 2.10 | | H | 2 | oil |
| 2.11 | | H | 0 | oil |
| 2.12 | | H | 2 | |
TABLE 2*)-continued
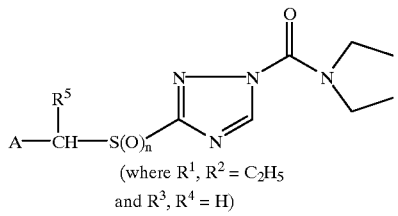
(where R¹, R² = C₂H₅ and R³, R⁴ = H)
| No. | A | R⁵ | n | mp [° C.] |
|---|---|---|---|---|
| 2.13 | | H | 1 | |
| 2.14 | | H | 2 | 108–109 |
| 2.15 | | H | 1 | |
| 2.16 | | H | 2 | 108–110 |
| 2.17 | | H | 0 | oil |
| 2.18 | | H | 2 | |
| 2.19 | | H | 0 | oil |
| 2.20 | | H | 2 | |
| 2.21 | | H | 1 | |

TABLE 2*)-continued
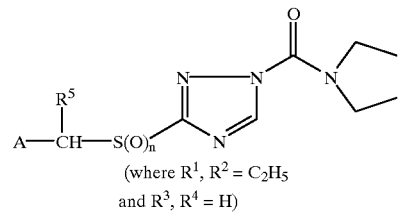
(where $R^1, R^2 = C_2H_5$ and $R^3, R^4 = H$)
| No. | A | $R^5$ | n | mp [°C.] |
|---|---|---|---|---|
| 2.22 | | H | 2 | |
| 2.23 | | H | 1 | |
| 2.24 | | H | 2 | oil |
| 2.25 | | $CH_3$ | 0 | oil |
| 2.26 | | $CH_3$ | 2 | 107–109 |
| 2.27 | | H | 0 | oil |
| 2.28 | | H | 2 | 87–88 |
| 2.29 | | H | 0 | |
| 2.30 | | H | 2 | oil |
| 2.31 | | H | 0 | oil |
| 2.32 | | H | 2 | |
TABLE 2*)-continued
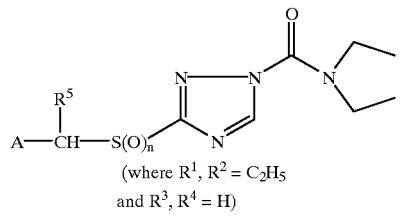
(where $R^1, R^2 = C_2H_5$ and $R^3, R^4 = H$)
| No. | A | $R^5$ | n | mp [°C.] |
|---|---|---|---|---|
| 2.33 | | H | 1 | |
| 2.34 | | H | 2 | |
| 2.35 | | H | 1 | |
| 2.36 | | H | 2 | oil |
| 2.37 | | H | 0 | |
| 2.38 | | H | 2 | |
| 2.39 | | H | 0 | oil |
| 2.40 | | H | 2 | 82–84 |
| 2.41 | | H | 0 | oil |

TABLE 2*)-continued

I (structure with R⁵, A-CH-S(O)ₙ- attached to triazole with N,N-diethylcarboxamide)

(where $R^1$, $R^2 = C_2H_5$ and $R^3$, $R^4 = H$)

| No. | A | $R^5$ | n | mp [° C.] |
|---|---|---|---|---|
| 2.42 | tetrahydrothiopyran-4-yl | H | 2 | |
| 2.43 | tetrahydrothiopyran-4-yl 1-oxide | H | 1 | |
| 2.44 | tetrahydrothiopyran-4-yl 1-oxide | H | 2 | |
| 2.45 | tetrahydrothiopyran-4-yl 1,1-dioxide | H | 1 | |
| 2.46 | tetrahydrothiopyran-4-yl 1,1-dioxide | H | 2 | 105–107 |
| 2.47 | 2,5-dihydrothiophen-3-yl | H | 0 | |
| 2.48 | 2,5-dihydrothiophen-3-yl | H | 2 | |
| 2.49 | 2,5-dihydrothiophen-3-yl 1-oxide | H | 1 | |
| 2.50 | 2,5-dihydrothiophen-3-yl 1-oxide | H | 2 | |
| 2.51 | 2,5-dihydrothiophen-3-yl 1,1-dioxide | H | 1 | |
| 2.52 | 2,5-dihydrothiophen-3-yl 1,1-dioxide | H | 2 | |
| 2.53 | 5,5-dimethyl-1,3-dioxan-2-yl | H | 0 | 60–61 |
| 2.54 | 5,5-dimethyl-1,3-dioxan-2-yl | H | 2 | 137–138 |
| 2.55 | 2-methyl-1,3-dioxolan-4-yl | H | 0 | |
| 2.56 | 2-methyl-1,3-dioxolan-4-yl | H | 2 | |
| 2.57 | 2-methyl-1,3-dioxolan-4-yl | H | 1 | |
| 2.58 | 2-(4-fluorobenzyl)-1,3-dioxolan-4-yl | H | 0 | oil |
| 2.59 | 2-(4-fluorobenzyl)-1,3-dioxolan-4-yl | H | 2 | 115–116 |
| 2.60 | 2,2-dimethyl-1,3-dioxolan-4-yl | H | 0 | oil |
| 2.61 | 2,2-dimethyl-1,3-dioxolan-4-yl | H | 2 | |

TABLE 2*)-continued (Structure I: A—CH(R⁵)—S(O)ₙ— connected to 1,2,4-triazole bearing —C(O)N(R¹)(R²) where R¹, R² = C₂H₅ and R³, R⁴ = H)

| No. | A | R⁵ | n | mp [°C.] |
|---|---|---|---|---|
| 2.62 | 4,6-dimethyl-1,3-dioxan-2-yl | H | 0 | |
| 2.63 | 4,6-dimethyl-1,3-dioxan-2-yl | H | 2 | |
| 2.64 | 4,6-dimethyl-1,3-dioxan-2-yl | H | 1 | |
| 2.65 | 1,3-dioxolan-2-yl | H | 0 | oil |
| 2.66 | 1,3-dioxolan-2-yl | H | 2 | 73–74 |
| 2.67 | 2-(4-phenylcyclohexyl)-1,3-dioxolan-2-yl | H | 0 | 90–91 |
| 2.68 | 2-(4-phenylcyclohexyl)-1,3-dioxolan-2-yl | H | 2 | 128–130 |
| 2.69 | 2,2-diphenyl-1,3-dioxolan-4-yl | H | 0 | oil |
| 2.70 | 2,2-diphenyl-1,3-dioxolan-4-yl | h | 2 | 123–124 |
| 2.71 | 3-(1-methoxyethyl)-5-methyl-4,5-dihydroisoxazol-5-yl | H | 0 | oil |
| 2.72 | 3-(1-methoxyethyl)-5-methyl-4,5-dihydroisoxazol-5-yl | H | 2 | oil |
| 2.73 | 2-[4-(2-methylprop-2-yl)phenyl]-1,3-dioxolan-4-yl | H | 0 | oil |
| 2.74 | 2-[4-(2-methylprop-2-yl)phenyl]-1,3-dioxolan-4-yl | H | 2 | |

*)The dotted line indicates the bonding position.

The triazoles of the formula II described above and other triazoles of the formula II which have been or can be prepared in a similar manner or in a manner known per se are listed in Table 3:

TABLE 3*)

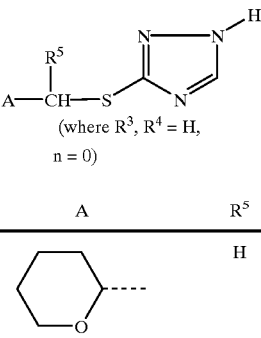

(where $R^3$, $R^4$ = H, n = 0)

| No. | A | $R^5$ | mp [° C.] |
|---|---|---|---|
| 3.01 | 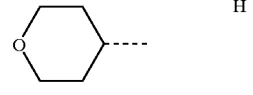 | H | oil |
| 3.02 | 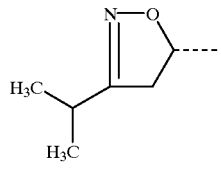 | H | oil |
| 3.03 | 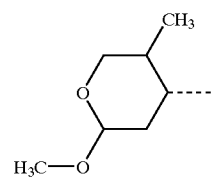 | H | oil |
| 3.04 | 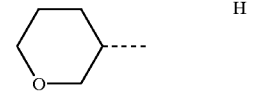 | H | |
| 3.05 | 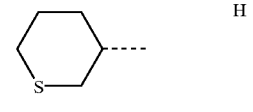 | H | oil |
| 3.06 | 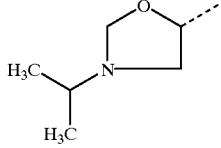 | H | oil |
| 3.07 | 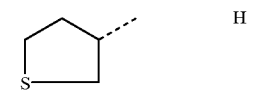 | H | |
| 3.08 | 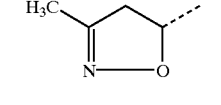 | H | oil |
| 3.09 | 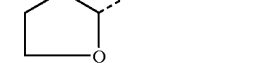 | $CH_3$ | oil |
| 3.10 | 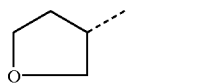 | H | |
| 3.11 | 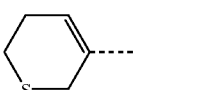 | H | |
| 3.12 | 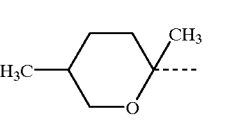 | H | |
| 3.13 | 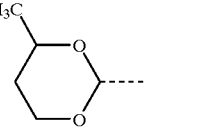 | H | |
| 3.14 | 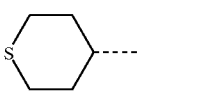 | H | |
| 3.15 | 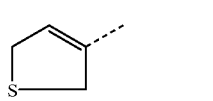 | H | |
| 3.16 | 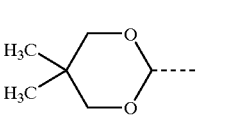 | H | |
| 3.17 | 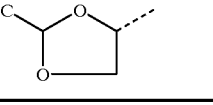 | H | 101–102 |
| 3.18 |  | H | |

*)The dotted line indicates the bonding position.

The compounds of the formula I and their agriculturally useful salts are suitable as herbicides and/or as bioregulators, both in the form of isomer mixtures and in the form of the pure isomers. The herbicidal compositions comprising compounds of the formula I are capable of controlling vegetation on non-crop areas very efficiently, especially at high rates of application. In crops such as wheat, rice, maize, soya and cotton, they act against broad-leaved weeds and grass weeds without causing any significant damage to the crop plants. This effect is observed mainly at low rates of application.

Depending on the application method employed, the compounds of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. altissima,

*Beta vulgaris* spec. rapa, *Brassica napus* var. napus, *Brassica napus* var. napobrassica, *Brassica rapa* var. silvestris, *Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays*.

In addition, the compounds of the formula I can also be used in crops which tolerate the action of herbicides owing to breeding including genetic engineering methods.

The compounds of the formula I, or the herbicidal compositions comprising them, can be used for example in the form of directly sprayable aqueous solutions, powders, suspensions, also highly concentrated aqueous, oily or other suspensions or dispersions, emulsions, oil dispersions, pastes, dusts, materials for spreading or granules by means of spraying, atomizing, dusting, spreading or watering. The use forms depend on the intended purposes; in any case, they should ensure the finest possible distribution of the active ingredients according to the invention.

Suitable inert additives are essentially: mineral oil fractions of medium to high boiling point, such as kerosine or diesel oil, further coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, alcohols, such as methanol, ethanol, propanol, butanol, cyclohexanol, ketones, such as cyclohexanone, or strongly polar solvents, eg. amines, such as N-methylpyrrolidone, or water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of a wetting agent, tackifier, dispersant or emulsifier. Alternatively, it is possible to prepare concentrates composed of active substance, wetting agent, tackifier, dispersant or emulsifier and, if desired, solvent or oil, these concentrates being suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and the salts of sulfated hexa-, hepta- and octadecanols and of fatty alcohol glycol ether, condensates of sulfonated naphthalene and its derivatives with formaldehyde, condensates of naphthalene, or of naphthalenesulfonic acids, with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methyl cellulose.

Powders, materials for spreading and dusts can be prepared by mixing or grinding the active substances with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active ingredients of the formula I in the ready-to-use preparations can be varied within wide ranges. In general, the formulations comprise from 0.001 to 98% by weight, preferably 0.01 to 95% by weight, of at least one active ingredient. The active ingredients are employed in a purity of from 90% to 100%, preferably 95% to 100% (according to NMR spectrum).

The following Formulation Examples illustrate the preparation of such preparations:

I. 20 parts by weight of the compound No. 2.02 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 2.04 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 2.06 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 2.11 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel and the mixture is ground in a hammermill. Finely distributing the mixture in 20,000 parts by weight of water gives a spray mixture which comprises 0.1% by weight of the active ingredient.

V. 3 parts by weight of the active ingredient No. 2.14 are mixed with 97 parts by weight of finely divided kaolin. This gives a dust which comprises 3% by weight of the active ingredient.

VI. 20 parts by weight of the active ingredient No. 2.02 are mixed intimately with 2 parts by weight of calcium dodecylbenzenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound 2.16 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound 2.26 is dissolved in a mixture composed of 80 parts by weight of cyclohexanone and 20 parts by weight of Wettol® EM 31 (=nonionic emulsifier based on ethoxylated castor oil; BASF AG). This gives a stable emulsion concentrate.

The active ingredients of the formula I or the herbicidal compositions can be applied pre- or post-emergence. If the active ingredients are less well tolerated by certain crop plants, application techniques may be used in which the herbicidal compositions are sprayed, with the aid of spraying apparatus, in such a way that they come into as little contact as possible, if any, with the leaves of the sensitive crop plants, while the active ingredients reach the leaves of undesirable plants which grow underneath, or the exposed soil surface (post-directed, lay-by).

Depending on the intended purpose, the season, the target plants and the growth stage, the rates of application of active ingredient of the formula I are from 0.001 to 3.0, preferably 0.01 to 1.0, kg of active substance (a.s.) per ha.

To widen the spectrum of action and to achieve synergistic effects, the substituted carbamoyl derivatives of the formula I can be mixed with a large number of representatives of other groups of herbicidal or growth-regulating active ingredients and applied jointly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids, and their derivatives, benzoic acid and its derivatives, benzothiadiazinones, 2-(het)aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Furthermore, it may be advantageous to employ the compounds of the formula I, on their own or in combination with other herbicides, also in a mixture with other crop protection agents, for example pesticides or agents for controlling phytopathogenic fungi or bacteria. Also of interest is the miscibility with mineral salt solutions which are employed for treating nutritional and trace element deficiencies. Nonphytotoxic oils and oil concentrates may also be added.

Use Examples

The herbicidal activity of the substituted carbamoyl derivatives of the formula I was demonstrated by greenhouse experiments:

The culture containers used were plastic flowerpots containing loamy sand with approximately 3.0% of humus as the substrate. The seeds of the test plants were sown separately for each species.

In the case of pre-emergence treatment, the active ingredients, which were suspended or emulsified in water, were applied directly after sowing by means of finely distributing nozzles. The containers were irrigated gently to promote germination and growth and subsequently covered with transluscent plastic hoods until the plants had rooted. This cover caused uniform germination of the test plants unless this was adversely affected by the active ingredients. The rate of application for the pre-emergence treatment was 3.0 kg of a.s./ha.

For the post-emergence treatment, the test plants were first grown to a plant height of from 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at from 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage or normal course of growth.

The plants used in the greenhouse experiments belong to the following species:

| Scientific Name | Common Name |
|---|---|
| *Echinochloa crus-galli* | barnyardgrass |
| *Lolium multiflorum* | annual ryegrass |

Using the pre-emergence method, the compounds 2.02 and 2.04 showed, at application rates of 3.0 kg/ha a.s., very good activity against the abovementioned harmful grasses.

We claim:

1. Substituted carbamoyltriazoles of the formula I

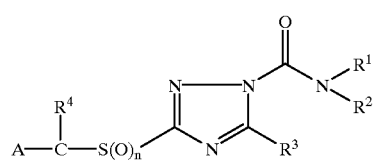

where
$R^1$ is hydrogen, $C_1$–$C_6$-alkyl, $C_1$–$C_6$-haloalkyl, $C_3$–$C_8$-cycloalkyl, $C_3$–$C_6$-alkenyl or $C_3$–$C_6$-alkynyl;
$R^2$ is $C_1$–$C_6$-alkoxy or $C_1$–$C_6$-haloalkoxy or a radical listed under $R^1$;

or

R$^1$ and R$^2$ together form a C$_2$–C$_5$-alkanediyl radical which may carry one to three substituents selected from the group consisting of halogen and C$_1$–C$_6$-alkyl and, in the case of a C$_4$–C$_5$-alkanediyl radical, a CH$_2$ group may be replaced by oxygen or a group NH or N-C$_1$–C$_6$-alkyl;

R$^3$, R$^4$, and R$^5$ are each hydrogen, cyano, C$_1$–C$_6$-alkyl, C$_1$–C$_6$-haloalkyl, C$_3$–C$_6$-cycloalkyl, C$_2$–C$_6$-alkenyl, C$_2$–C$_6$-alkynyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylcarbonyl, C$_1$–C$_6$-haloalkylcarbonyl, C$_1$–C$_6$-alkoxycarbonyl, phenyl or benzyl, where the last two substituents may be partially or fully halogenated and may carry one to three of the following groups:
nitro, cyano, C$_1$–C$_4$-alkyl, C$_1$–C$_4$-haloalkyl, C$_1$–C$_4$-alkoxy, C$_1$–C$_4$-haloalkoxy and
C$_1$–C$_4$-alkoxycarbonyl;

A is an unsubstituted or substituted saturated or partially unsaturated five- or six-membered heterocycle having oxygen or sulfur atoms or a five-membered heterocycle having one or two nitrogen or one nitrogen and one oxygen atoms;

n is 0, 1 or 2;
with the proviso that A is not 1,3-dioxolan-2-yl or 1,3-dioxan-2-yl;
and the agriculturally useful salts of I.

2. Substituted carbamoyltriazoles of the formula I as claimed in claim 1, where

A is a five-membered saturated or partially unsaturated heterocycle having oxygen or sulfur atoms or two nitrogen or one nitrogen and one oxygen atom and which carries attached to carbon, one to three radicals selected from the group consisting of R$^6$, R$^7$ and R$^8$, where any ring nitrogen may, independently of any other(s), carry a radical R$^{10}$; or is a six-membered saturated or partially unsaturated heterocycle having oxygen or sulfur atoms and which carries, attached to carbon, one to four radicals selected from the group consisting of R$^6$, R$^7$, R$^8$ and R$^9$, where any ring nitrogen may, independently of any other(s), carry a radical R$^{10}$;

R$^6$, R$^7$, R$^8$ and R$^9$ are each cyano, halogen, C$_1$–C$_6$-alkyl, C$_1$–C$_6$-haloalkyl, C$_3$–C$_6$-cycloalkyl, C$_2$–C$_6$-alkenyl, C$_2$–C$_6$-alkynyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylcarbonyl, C$_1$–C$_6$-haloalkylcarbonyl, C$_1$–C$_6$-alkoxycarbonyl, phenyl or benzyl where the last two substituents may be partially or fully halogenated and/or may carry one to three of the following groups:
nitro, cyano, C$_1$–C$_4$-alkyl, C$_1$–C$_4$-haloalkyl, C$_1$–C$_6$-alkoxy, C$_1$–C$_6$-haloalkoxy and
C$_1$–C$_4$-alkoxycarbonyl;

R$^{10}$ is C$_1$–C$_6$-alkyl, C$_1$–C$_6$-haloalkyl, C$_3$–C$_6$-cycloalkyl, C$_3$–C$_6$-alkenyl, C$_3$–C$_6$-alkynyl, C$_1$–C$_6$-alkylcarbonyl, C$_1$–C$_6$-haloalkylcarbonyl, C$_1$–C$_6$-alkoxycarbonyl, phenyl or benzyl where the last two substituents may be partially or fully halogenated and/or may carry one to three of the following groups:
nitro, cyano, C$_1$–C$_4$-alkyl, C$_1$–C$_4$-haloalkyl, C$_1$–C$_4$-alkoxy, C$_1$–C$_4$-haloalkoxy and
C$_1$–C$_4$-alkoxycarbonyl.

3. Substituted carbamoyltriazoles of the formula I as claimed in claim 1 where

R$^1$ and R$^2$ are each C$_1$–C$_6$-alkyl.

4. Substituted carbamoyltriazoles of the formula I as claimed in claim 1 where

R$^3$ and R$^4$ are each hydrogen.

5. A process for preparing substituted carbamoyltriazoles of the formula I as claimed in claim 1, which comprises reacting a triazole of the formula II

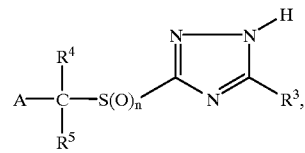

with a carbamoyl halide of the formula III

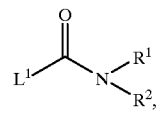

where R$^1$ to R$^5$, A and n are each as defined in claim 1 and L$^1$ is halogen.

6. A process for preparing substituted carbamoyltriazoles of the formula I where n=1 or 2 as claimed in claim 1, wherein a substituted carbamoyltriazole of the formula I where n=0 as claimed in claim 1

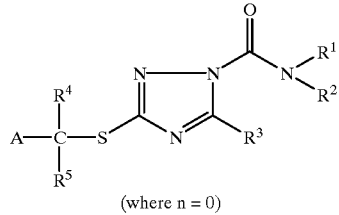

(where n = 0)

is treated with an oxidizing agent where R$^1$ to R$^5$ and A each are as defined in claim 1.

7. Triazoles of the formula II

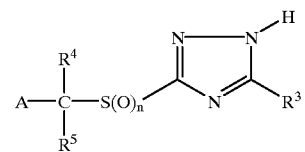

where

R$^3$, R$^4$, and R$^5$ are each hydrogen, cyano, C$_1$–C$_6$-alkyl, C$_1$–C$_6$-haloalkyl, C$_3$–C$_6$-cycloalkyl, C$_2$–C$_6$-alkenyl, C$_2$–C$_6$-alkynyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylcarbonyl, C$_1$–C$_6$-haloalkylcarbonyl, C$_1$–C$_6$-alkoxycarbonyl, phenyl or benzyl, where the last two substituents may be partially or fully halogenated and may carry one to three of the following groups:
nitro, cyano, C$_1$–C$_4$-alkyl, C$_1$–C$_4$-haloalkyl, C$_1$–C$_4$-alkoxy, C$_1$–C$_4$-haloalkoxy and
C$_1$-C$_4$-alkoxycarbonyl;

A is an unsubstituted or substituted saturated or partially unsaturated five- or six-membered heterocycle having oxygen or sulfur atoms or a five-membered heterocycle having one or two nitrogen or one nitrogen and one oxygen atom;

n is 2;

with the proviso that A is not 1,3-dioxolan-2-yl or 1,3-dioxan-2-yl.

8. A herbicidal composition comprising a herbicidally active amount of at least one substituted carbamoyltriazole of the formula I as claimed in claim 1 or of an agriculturally useful salt thereof and at least one inert liquid and/or solid carrier and, if desired, at least one surfactant.

9. A process for preparing herbicidally active compositions as claimed in claim 8, which comprises mixing a herbicidally active amount of at least one substituted carbamoyltriazole of the formula I or of an agriculturally useful salt thereof and at least one inert liquid and/or solid carrier and, if desired, at least one surfactant.

10. A method of controlling undesirable vegetation, which comprises allowing a herbicidally active amount of at least one substituted carbamoyltriazole of the formula I as claimed in claim 1 or of an agriculturally useful salt thereof to act on plants, their habitat or on seeds.

* * * * *

UNITED STATES PATENT AND TRADEMARK OFFICE
CERTIFICATE OF CORRECTION

PATENT NO. : 6,265,352 B1
DATED : July 24, 2001
INVENTOR(S) : Baumann et al.

It is certified that error appears in the above-identified patent and that said Letters Patent is hereby corrected as shown below:

<u>Column 42,</u>
Line 53, "carbarnoyltriazoles" should be -- carbamoyltriazoles --.

Signed and Sealed this

Twenty-fifth Day of October, 2005

JON W. DUDAS
*Director of the United States Patent and Trademark Office*